(12) United States Patent
Chen et al.

(10) Patent No.: US 9,309,577 B2
(45) Date of Patent: Apr. 12, 2016

(54) PROCESS FOR PRODUCING BIO-BASED PRODUCT FROM STRAW HEMICELLULOSE AND FULLY UTILIZING THE COMPONENTS THEREOF

(75) Inventors: Hongzhang Chen, Beijing (CN); Lan Wang, Beijing (CN)

(73) Assignee: Institute of Process Engineering, Chinese Academy of Sciences, Beijing (CN)

( * ) Notice: Subject to any disclaimer, the term of this patent is extended or adjusted under 35 U.S.C. 154(b) by 168 days.

(21) Appl. No.: 13/992,381

(22) PCT Filed: Jan. 28, 2011

(86) PCT No.: PCT/CN2011/000142
§ 371 (c)(1),
(2), (4) Date: Jun. 7, 2013

(87) PCT Pub. No.: WO2012/100375
PCT Pub. Date: Aug. 2, 2012

(65) Prior Publication Data
US 2013/0252293 A1    Sep. 26, 2013

(51) Int. Cl.
| | |
|---|---|
| *C12P 7/56* | (2006.01) |
| *C12P 7/54* | (2006.01) |
| *C13K 13/00* | (2006.01) |
| *C07D 307/48* | (2006.01) |
| *C07D 307/50* | (2006.01) |
| *C08H 8/00* | (2010.01) |
| *C12P 3/00* | (2006.01) |
| *C12P 5/02* | (2006.01) |
| *C12P 7/16* | (2006.01) |
| *C12P 7/18* | (2006.01) |
| *C12P 7/46* | (2006.01) |
| *C07C 51/00* | (2006.01) |
| *C08B 11/08* | (2006.01) |
| *C08B 37/00* | (2006.01) |
| *C08H 7/00* | (2011.01) |
| *C12N 1/20* | (2006.01) |
| *C13K 1/02* | (2006.01) |
| *D21C 1/02* | (2006.01) |
| *D21C 3/04* | (2006.01) |
| *D21H 11/12* | (2006.01) |

(52) U.S. Cl.
CPC ............... *C13K 13/00* (2013.01); *C07C 51/00* (2013.01); *C07D 307/48* (2013.01); *C07D 307/50* (2013.01); *C08B 11/08* (2013.01); *C08B 37/0003* (2013.01); *C08B 37/0057* (2013.01); *C08H 6/00* (2013.01); *C08H 8/00* (2013.01); *C12N 1/20* (2013.01); *C12P 3/00* (2013.01); *C12P 5/023* (2013.01); *C12P 7/16* (2013.01); *C12P 7/18* (2013.01); *C12P 7/46* (2013.01); *C12P 7/54* (2013.01); *C12P 7/56* (2013.01); *C13K 1/02* (2013.01); *C13K 13/002* (2013.01); *C12P 2201/00* (2013.01); *C12P 2203/00* (2013.01); *D21C 1/02* (2013.01); *D21C 3/04* (2013.01); *D21H 11/12* (2013.01); *Y02E 50/10* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 2,481,263 A | 9/1949 | Tsuchiya et al. | |
| 4,424,275 A | 1/1984 | Levy | |
| 4,539,293 A | 9/1985 | Bergstrom et al. | |
| 4,649,112 A | 3/1987 | Datta et al. | |
| 4,777,135 A | 10/1988 | Husted et al. | |
| 5,063,156 A | 11/1991 | Glassner et al. | |
| 6,409,841 B1 | 6/2002 | Lombard | |
| 8,030,040 B2* | 10/2011 | Hughes | 435/165 |
| 2009/0229599 A1* | 9/2009 | Zhang | 127/1 |
| 2010/0279361 A1 | 11/2010 | South et al. | |
| 2011/0081689 A1* | 4/2011 | Flanegan et al. | 435/105 |

FOREIGN PATENT DOCUMENTS

| | | | |
|---|---|---|---|
| CN | 101358214 | | 2/2009 |
| CN | 101358218 | | 2/2009 |
| CN | 101358218 A | * | 4/2009 |
| CN | 101434968 | | 5/2009 |
| CN | 101942485 | | 1/2011 |

OTHER PUBLICATIONS

Ruiz et al., Enzyme and Microbial Technology, 42:160-166, 2008.*
Khan et al., International Journal of Adhesion & Adhesives 24:485-493, 2004.*
Wang et al., "Increased Fermentability of Enzymatically Hudrolyzed Steam-Exploded Corn Stover for Butanol Production by Removal of Fermentation Inhibitors," Process Biochemistry, 46:604-607 (2011).

* cited by examiner

*Primary Examiner* — Jennifer Pitrak McDonald
*Assistant Examiner* — Qing Xu
(74) *Attorney, Agent, or Firm* — Cesari and McKenna LLP

(57) ABSTRACT

Provided is a process for producing biomass-based product from straw hemicellulose and utilizing the components thereof thoroughly. Steam-explosion and acid-hydrolysis are combined in the pre-treatment of straw in the process, thus a higher concentration of a sugar liquid can be obtained, and furfural and acetic acid can be recovered. The hemicellulose obtained by the pre-treatment can be used directly as ferment materials for producing butanol, succinic acid, butylene glycol, lactic acid, hydrogen and firedamp, which reduces the cost of these biomass-based products. The cellulose and lignin obtained by extracting the straw with an alkaline solution can produce products, such as sodium hydroxymethyl cellulose etc. In the process, all components in the straw can be utilized thoroughly and waste and pollutant will not be produced.

12 Claims, 2 Drawing Sheets

PROCESS FOR PRODUCING BIO-BASED PRODUCT FROM STRAW HEMICELLULOSE AND FULLY UTILIZING THE COMPONENTS THEREOF

CROSS REFERENCE TO RELATED APPLICATIONS

This application is a National Stage of International Application No. PCT/CN2011/000142 filed on Jan. 28, 2011, the contents of which are hereby incorporated by reference in their entirety.

TECHNICAL FIELD

The present invention belongs to the field of the comprehensive utilization of straw resources, and particularly relates to a process for producing a bio-based product from straw hemicellulose and fully utilizing the components thereof.

BACKGROUND ART

China is a major petroleum import country, and about 50 percent of petroleum is imported each year. Besides the majority of the petroleum resource is used as fuels for production and refining, there is also a considerable part of the petroleum resource used for the production of chemicals.

With the gradual depletion of petroleum resources, the focus of energy research has been shifted to biofuels in the whole world. In addition to the clean energy sources such as methane and hydrogen, biofuels-butanol wins the favor of more people and is known as the third-generation biofuels, because of its advantages, such as capable of being mixed with gasoline in any ratio, not requiring any reconstruction for vehicles, having high economic value, effectively improving the fuel efficiency and mileage of vehicles, and so on. At the aspect of bio-based chemicals, attention has been widely paid to some of the key platform compounds, such as 2,3-butanediol currently, which as an additive, can be widely applied to inks, cosmetics, lotions, plasticizers, drug and other industries, but also has the performance of liquid fuels. In addition, lactic acid, as an important chemical, is also widely used in the processing of food, pharmaceutical, cosmetics, chemical materials and agricultural products. At present, most of these bio-based products are produced from corn, wheat and other starch materials as the major raw materials through a saccharification and fermentation process. However, the production of biofuels from food supplies not only cannot meet the needs of the community, but also will endanger food safety. It was reported by some researchers that even if all the corn and soybeans grown in the United States were used for the production of bio-energy, only 12% of U.S. gasoline demand and 6% of U.S. diesel oil demand could be satisfied. In fact, corn and soybeans cannot be all used to produce biofuels, because their priority use is for foodstuff, feedstuff and other economic needs.

China has very rich straw resources. Its annual output is about 700 million tons. However, most of the straws have not been effectively utilized till now. If we can use bio-refining technologies to produce chemicals, materials and fuels from straws, as the main raw material, the petroleum import pressure can be sufficiently alleviated in China. Therefore, exploring the fermentation of non-foodstuff plants such as straws, as the raw materials is an important route to achieve the sustainable production of bio-based products.

The main components of the cell walls of straws include cellulose, hemicellulose and lignin. Lignin together with hemicellulose are filled as an intercellular substance between the microfine fibers in the cell walls, reinforce the cell walls of the wood tissue, and are also present in the intercellular layer to allow the adjacent cells to be bonded together. Cellulose, as a chained polymer of glucoside linked by beta-1,4-glycosidic bond, can be used for the production of all kinds of chemical and material products, and can also be biodegraded into glucose for the production of a variety of fermentation products. Hemicellulose is a general designation for a large class of polysaccharides having different structures, such as pentosan, poly-arabinose, polymannose, polygalactose, wherein the main component is pentosan. The degradation products of hemicellulose mainly include xylose, arabinose, mannose, and a small amount of glucose, can be converted by microbes into biofuels such as ethanol, butanol, methane and hydrogen, and can also be fermented into butanediol, xylitol, lactic acid and single-cell protein. Lignin, as an important chemical product itself, is a class of complex amorphous materials of phenylpropanes units linked by ether bonds and carbon-carbon-bonds.

Currently, the main problems up against the use of straw to produce biofuels include the high costs for raw material pretreatment and enzymatic hydrolysis, as well as the low utilization value of the raw materials. The reasons for that are shown as follows. First, people tend to only pay attention to the use of the cellulose that is difficult to be degraded in straw, but turn a blind eye to the hemicellulose resource in an amount of 25%-35% of straw. In fact, steam explosion pretreatment and dilute acid pretreatment can be used to effectively degrade and remove hemicelluloses but remain lignin and cellulose. Then after an alkali treatment, the lignin and cellulose can be obtained. Straw cellulose, due to its special chemical structure, has a great market value in the material product industry. However, in practice, people tend to degrade straw cellulose completely, while ignoring its functional features, thus resulting in the high degradation cost and low production value. In addition, the lignin in straw is often used as fuel for direct combustion. Nevertheless, in fact, the processed lignin can be made into a chemical raw material with a high added value.

Comparison of the disclosed invention patents is shown as follows. U.S. Pat. No. 2,481,263 discloses a process of direct fermentation of acetone, butanol and ethanol from pentose acid hydrolyzate. The key innovation of this invention is that fine iron powder and limestone are used for the detoxification of the acid hydrolyzate, then the xylose solution is fermented after flash-steam sterilization. In this patent, a great amount of iron powder and limestone are required in the detoxification process, and no comprehensive utilization of the raw materials is taken into consideration. Therefore, as the environmental pressure increases gradually, it cannot be used for industrial production apparently. U.S. Pat. No. 4,424,275 discloses a method of the continuous production using butanol, characterized in that butanol is first continuously extracted by a solvent extraction method, and then the extraction solvent is recycled in combination with distillation. Although this patent involves some innovation to the fermentation method, the issues regarding the raw materials are barely considered. U.S. Pat. No. 4,539,293 discloses a method of co-fermenting *Clostridium pasteurianum* and *C. Butylicum*, so as to improve butanol production and the proportion of the butanol in the solvent. However, no innovation was made to the raw materials for fermentation. U.S. Pat. No. 4,649,112 discloses a method of directly fermenting corn bran fiber or a mixture of corn bran fiber and xylan to obtain butanol by *C. acetobutylicum*. Although the pre-hydrolysis step is omitted in this method, the fermentation microbes mainly utilize the starch contained in the raw materials for fermentation, which also limits the types of raw materials for butanol fermentation. U.S. Pat. No. 4,777,135 discloses a method to promote butanol fermentation by adding a fluorocarbon compound in the butanol fermentation broth. However, this patent barely involves the source of the raw materials. U.S. Pat. No. 5,063, 156 ameliorates butanol fermentation from the point of view of the fermentation methods, and improves the proportion of butanol in all the products during the butanol fermentation process by means of the combination of continuous fermentation and batch fermentation. Chinese Patent with Publication No. CN 101434968A discloses a method for producing fuel butanol from tapioca. Even though cassava is a non-food raw materials, the cultivation of cassava still requires vast lands. It was also reported that since the production of cassava alcohol began in Guangxi, the price of cassava has been highly raised, which causes the cost of cassava alcohol is higher than its market price. In this case, the same problem will also be faced by the production of butanol from cassava. Therefore, the exploration of butanol production from straw-cellulose raw materials will be a better production route. Chinese Patent with Publication No. CN101358218A discloses a method to produce pentose together with acetone, butanol and ethanol from straw. Chinese Patent with Publication No. CN101358214A discloses a method to produce furfural together with acetone and butanol from straw. In both of these patents, straw is used as the raw material; after hydrolysis, the hemicelluloses in the straw is converted into five-carbon sugar or furfural; the remaining hydrolyzate is, after treated, converted into glucose through enzymolysis; then fermentation is conducted to produce butanol. Although by this method butanol can be produced, now it seems that the degradation of cellulose to glucose requires cellulase, which involves a very high production cost. As a result, using this route to the production of butanol, the production cost is high. When the butanol is used as a fuel, the price cannot be accepted by the market.

Therefore, it is desired to find a cheaper and easier process for pretreating raw materials, so as to improve the efficiency of utilization and degradation of straw, improve product yield and reduce production costs at the same time.

DISCLOSURE OF THE INVENTION

Due to the high cost for the degradation of straw cellulose, as well as the resulted high cost for the fermentation of products such as biofuels, etc., an object of the present invention is to provide an improved straw pretreatment method, so as to provide a new route for the production of low-cost straw fermentation product and achieve the high-value utilization of straw resources.

To achieve this object, the present inventors have carried out extensive research work, and found that hemicellulose can be directly used as a raw material for fermentation, so as to reduce the cost of production of bio-based products and to simplify the utilization of cellulose and lignin by using its characteristics which is susceptible to be degraded by steam explosion pretreatment and dilute acid pretreatment. At the same time, the inventors unexpectedly found that when straw is pretreated in a combination of steam explosion and dilute acid in a certain condition, a better utilization of straw can be achieved.

Accordingly, the present invention includes three aspects: the degradation of the straw hemicellulose, the preparation of bio-based products from a straw hemicellulose degradation liquid, and the separation of the cellulose and lignin of straw.

In a first aspect, the present invention is to provide a method of degrading straw hemicellulose, and the method comprises two treating modes: (1) water immersion, steam explosion treatment in combination with acid treatment; and (2) acid soak in combination with steam explosion treatment.

The mode which involves water immersion, steam explosion treatment in combination with acid treatment includes the following steps:
1) straw pretreatment: straw is soaked in water;
2) steam explosion process: the straw soaked in step 1) is fed into a steam-explosion tank and maintained under a steam-explosion pressure for a steam-explosion period; then the steam-exploded straw material is released;
3) acid treatment: the steam-exploded straw material obtained in step 2) is fed into an acid-hydrolysis tank pre-filled with a dilute acid and subjected to acid hydrolysis to generate a hydrolyzed material; and
4) product collection: after acid hydrolysis, the hydrolyzed material obtained in step 3) is filtered to generate a hydrolyzate liquid, and the hydrolysis residue is collected and extruded using an extruder to obtain a solid material.

The mode which involves acid soak in combination with steam explosion treatment includes the following steps:
1) straw pretreatment: straw is soaked in a dilute acid;
2) steam explosion process: the straw soaked in step 1) is fed into a steam-explosion tank and maintained under a steam-explosion pressure for a steam-explosion period; then the steam-exploded wet straw material is released; and
3) product collection: the steam-exploded wet straw material in step 2) is added to and soaked in water thoroughly, the steam-exploded wet straw material is extruded using an extruder to obtain a solid material, and the extrusion liquid is collected simultaneously and filtered to generate a clarified hydrolyzate liquid.

In a second aspect, the present invention is to provide a method of preparing bio-based products from a straw hemicellulose degradation liquid, and the method comprises the following steps of:
a) distilling the hydrolyzate liquid obtained by the method according to the invention under a reduced pressure, collecting and refining the distillate to obtain furfural and acetic acid, wherein the distilled residue liquid is a sugar solution; and
b) preparing a fermentation medium from the sugar solution obtained in step a) after detoxification treatment by adding nitrogen source therein, inoculating and culturing a seed solution of a fermentation bacterium in the logarithmic growth phase.

In a third aspect, the present invention is to provide a method of separating cellulose and lignin of straw, and the method comprises the following steps:
1) the solid material obtained from the extrusion of the steam-exploded straw is fed to an alkaline extraction tank and incubated at a temperature of 150° C. for 4 h upon the addition of a 2 wt % NaOH solution; a solid material is extruded using an extruder and alkaline extraction liquid and alkaline extraction residue are obtained; the alkaline extraction liquid passes through a PVC ultrafiltration membrane to recover NaOH; the solid material obtained by ultrafiltration is collected and dried to obtain lignin;
2) the lignin is used for the production of phenolic resin adhesive, a phenolic resin, a rubber reinforcing agent, a nano-carbon fiber; and 3) the alkaline extraction residue passes through a mechanical carding machine to separate long fibers and short fibers, wherein the long fibers are used for the production of sodium hydroxymethyl cellulose and polyether polyols and the short fibers are degraded into glucose while cellulase is added.

The present invention has the following beneficial effects:

1 The pretreatment of straw by combination of steam explosion and acid hydrolysis allows the hemicelluloses contained therein to be sufficiently released into the hydrolyzate liquid, increases the yield of furfural and acetic acid and the concentration of the sugar solution, and also can improve efficiency of producing all kinds of fermentation products from the sugar solution.

2. The direct utilization of the easily degraded hemicellulose in straw as a fermentation raw material to produce a fermentation product such as butanol, etc. avoid the problem in prior art (see the butanol fermentation routes disclosed in CN101358218A and CN101358214A), i.e. a great amount of cellulase is required for the fermentation of butanol from glucose obtained by cellulose enzymolysis. As a result, the raw-material cost for butanol can be effectively reduced, and a very good solution is provided to the issue in prior art (see U.S. Pat. No. 4,649,112 and the Chinese invention patent CN10143968A), i.e. only corn bran fiber, or a mixture of corn bran fiber and xylan or tapioca can be used in butanol fermentation methods.

3 No waste or pollution is generated during the whole process. All components of straw are subjected to a high-value utilization (see FIG. 1 for the process). Lignin can be used for the production of phenolic resin adhesive, a phenolic resin, a rubber reinforcing agent, a nano-carbon fiber. Cellulose can be used for the production of sodium hydroxymethyl cellulose, bio-polyether polyol and materials. In the present invention, cellulose and lignin are obtained by alkaline extraction and removal of straw hemicelluloses, these cellulose and lignin are different from the cellulose and lignin derived from traditional paper making methods. Because the alkali is in a small amount and extraction period is short, the lignin prepared by the present invention has a high purity and uniform molecular weight, and is conducive to liquefaction into a polyether polyol and phenolic resin.

DESCRIPTION OF THE PREFERRED EMBODIMENTS

The present invention is to provide a process of producing bio-based products from the degradation liquid of straw hemicellulose (hereinafter referred to as "the method of the present invention"), and this method comprises three steps of degrading straw hemicelluloses; producing bio-based products from the degradation liquid of straw hemicelluloses; and separating cellulose and lignin of straw.

Figure 2:
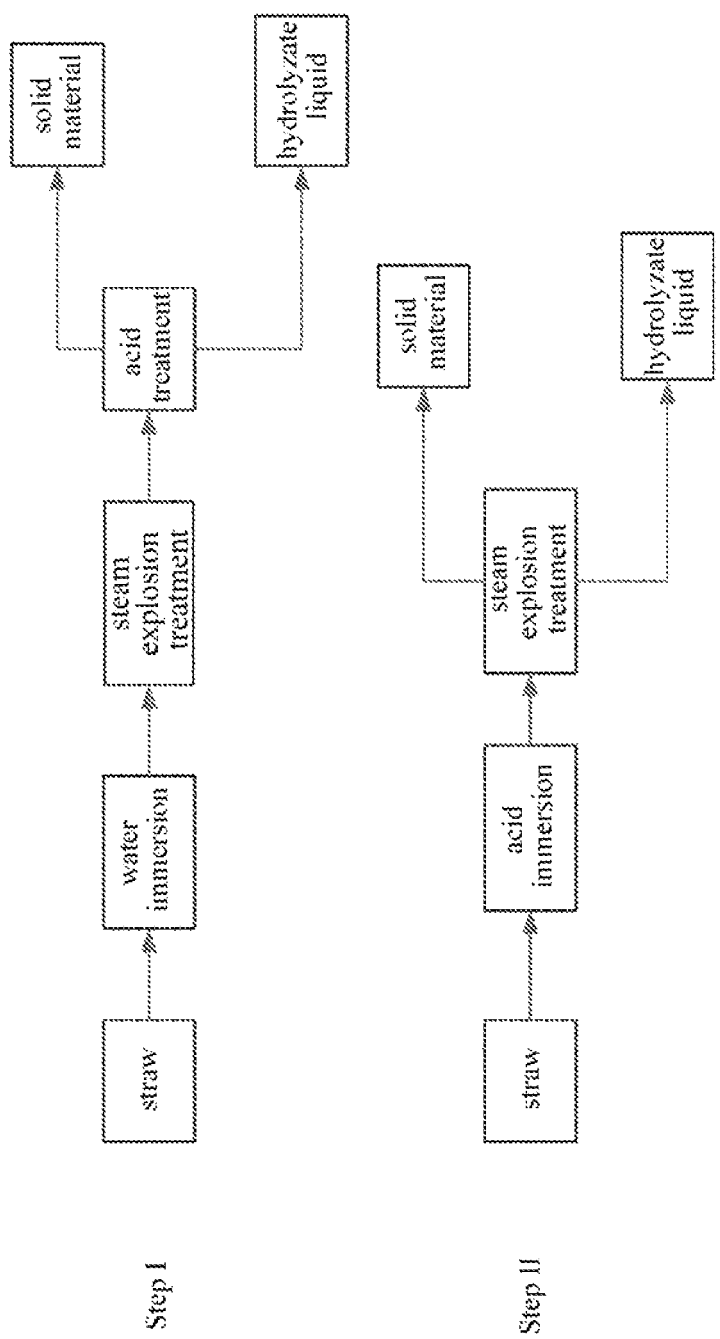
FIG. 2 shows the steps in the two embodiments of degradation of straw hemicellulose provided in the present invention.

In the method of the present invention, the degradation of the straw hemicellulose can be carried out by two approaches, see Step I and Step II in FIG. 2.

In the Step I shown in FIG. 2 (i.e. water immersion, steam explosion treatment in combination with acid treatment), the processing of straw includes the following steps: first, straw is soaked in water for a period of time and then subjected to steam-explosion treatment after fed into a steam-explosion tank; the obtained steam-exploded straw is then fed into an acid-hydrolysis tank and subjected to an acid treatment therein. After the acid treatment, the steam-exploded straw and hydrolyzate liquid are separated through a plate filter to generate a steam-exploded straw hydrolyzate liquid and a steam-exploded straw solid material.

Accordingly, in the first embodiment of the present invention, the method of the present invention comprises the following steps:

1) pretreating straw, wherein the straw is soaked in water, wherein the mass ratio of straw to water is 1:1 to 1:3, the soaking temperature is 15° C. to 90° C., and the soaking period is 10 mins to 60 mins;

2) conducting steam explosion, wherein the straw soaked in step 1) is fed into a steam-explosion tank, and maintained under a certain steam-explosion pressure for a steam-explosion period; then the steam-exploded straw material is released, wherein the steam-explosion pressure is 0.3 MPa to 2.0 MPa, preferably 0.5 to 1.0 MPa, and the pressure maintenance period is 1 mins to 10 mins;

3) performing an acid treatment, wherein the steam-exploded straw material obtained in step 2) is fed into an acid-hydrolysis tank pre-filled with a 0.8 to 1.6% dilute acid and subjected to acid hydrolysis to generate a hydrolyzed material, wherein in the acid-hydrolysis tank, the mass ratio of the steam-exploded straw to the dilute acid is 1:2 to 1:7, the reaction temperature is 75° C. to 105° C., and the reaction time is 10 mins to 60 mins; and 4) collecting the product, wherein after acid hydrolysis, the hydrolyzed material obtained in step 3) is filtered to generate a hydrolyzate liquid, and the hydrolysis residue is collected and extruded using an extruder to obtain a solid material.

In the Step II shown in FIG. 2 (i.e. acid soak in combination with steam explosion treatment), the processing of straw includes the following steps: first straw is soaked in a dilute acid for a period of time and then subjected to steam-explosion treatment after fed into a steam-explosion tank. The resultant steam-exploded wet straw material is passed through an extruder to separate a steam-exploded straw hydrolyzate liquid and a steam-exploded straw solid material.

Accordingly, in the second embodiment of the present invention, the method of the present invention comprises the following steps:

1) pretreating straw, wherein the straw is soaked in a dilute acid, wherein the mass ratio of straw to the dilute acid is 1:1 to 1:3, the concentration of the dilute acid is from 0.01 to 0.1 wt %, preferably from 0.02 to 0.05 wt %, and the soaking period is 10 mins to 60 mins;

2) conducting steam explosion, wherein the straw soaked in step 1) is fed into a steam-explosion tank, and maintained under a steam-explosion pressure for a steam-explosion period; then the steam-exploded wet straw material is released, wherein the steam-explosion pressure is 0.3 MPa to 1.0 MPa, and the pressure maintenance period is 0.5 min to 3 mins; and 3) collecting the product, wherein the steam-exploded wet straw material in step 2) is added to and soaked in water in the weight equal to 4-10 times of that of the dry straw material at 70° C. for 30 mins to 1 h, the steam-exploded wet straw material is extruded using an extruder to obtain a solid material, and the extrusion liquid is collected simultaneously and filtered to generate a clarified hydrolyzate liquid.

The main components of straw include cellulose, hemicellulose and lignin, wherein the first two components can be degraded into monosaccharides for production of butanol through fermentation. However, the degradation of cellulose requires a rigorous condition, and consumption of a large amount of cellulase is necessary for its effective degradation. As such, production of butanol and other chemicals from the hexose in straw faces the pressure of high costs. However, since straw hemicellulose is susceptible to degradation, it can be sufficiently degraded into monosaccharides by way of steam explosion or dilute acid treatment, then the monosaccharides can utilized by bacteria to produce butanol, butanediol, lactic acid, methane, hydrogen and other products. After the removal of hemicellulose from straw, the residue can be subjected to an alkaline treatment to effectively separate cellulose and lignin. The obtained cellulose and lignin can, after appropriate processing, be converted into cellulose derivatives and lignin derivatives with high added values.

Therefore, the straw used in the method of the present invention can be selected from a very large scope, for example, can be one or more selected from corn straw, rice straw, wheat straw, bagasse, corn cobs, sorghum straw, *miscanthus sinensis, imperata cylindrica*, ramie, jute, abutilon, marijuana, flax, Apocynum, kenaf, cotton stalks, banana stems, pineapple leaf, or *ponnisetum hydridum*. Among others, from the point of view of the hemicellulose content, corn straw, corn cobs, bagasse and marijuana are preferred.

In the embodiments described above, in the step 1) of pretreating straw, air-dried straw (water content is less than 3%) is generally cut into small pieces in the size of 3-10 cm.

In the embodiments described above, the dilute acid is typically selected from inorganic acids, such as one or more selected from the group consisting of dilute sulfuric acid, dilute hydrochloric acid, dilute nitric acid, and dilute phosphoric acid. A person skilled in the art can make the appropriate choices according to the specific process conditions, the cost of raw materials and other factors.

In another embodiment of the present invention, the method of the present invention further comprises the following steps of a) distilling the hydrolyzate liquid obtained by the method of the present invention under a reduced pressure, collecting and refining the distillate to obtain furfural and acetic acid, wherein the distilled residue liquid is a sugar solution at a concentration of 20 g/L 150 g/L by weight of xylose and glucose; and b) adding the sugar solution obtained in step a) to a fermentation medium made from nitrogen source after a detoxification treatment, and inoculating a seed solution of a fermentation bacterium in the logarithmic growth phase at a concentration of 10% by weight of the medium, wherein the detoxification treatment is one or more selected from the group consisting of electrodialysis, macroporous resin adsorption and activated carbon adsorption, the nitrogen source is one or more selected from the group consisting of corn milk, corn extracts, yeast extract, peptone, $(NH_4)_2HPO_4$, $(NH_4)_2SO_4$ and ammonium acetate, and the fermentation bacterium is *Clostridium acetobutylicum, Actinobacillus succinogenes, Klebsiella, Lactobacillus* or *Clostridium butyricum*.

In a preferred embodiment, the processing condition for the electrodialysis includes a temperature of 15 to 30° C. and a current density of 600~1000 A/m$^2$; the processing condition for the macroporous resin adsorption includes a volume ratio of 1:3 to 1:10 between the sugar solution and the macroporous resin and a processing period of 4~12 h; the processing condition for the activated carbon adsorption includes a volume ratio of 1:3 to 1:10 between the sugar solution and the activated carbon and a processing period of 4~12 h. Among others, the macroporous resin can be selected from the group consisting of macroporous adsorption resin AB-8 with a weak polarity; activated carbon particles are in the size of 20-40 mesh; and iodine adsorption value: ≥1000.

In addition, for the purpose of more efficient and high-value utilization of straw, the solid material obtained in the method of the present invention can also be fed to the alkaline extraction tank; a 0.2%~10% NaOH solution is added and kept at a temperature of 130° C. to 200° C. for 0.5 h~4 h; solid-liquid separation is conducted to obtain an alkaline extraction residue and an alkaline extraction liquid; the extraction liquid passes through the an ultrafiltration membrane for collecting the solid material obtained by the ultrafiltration; the collected solid material is lignin with a high purity; the alkaline extraction residue is combed mechanically to separate long fibers and short fibers.

Figure 1:
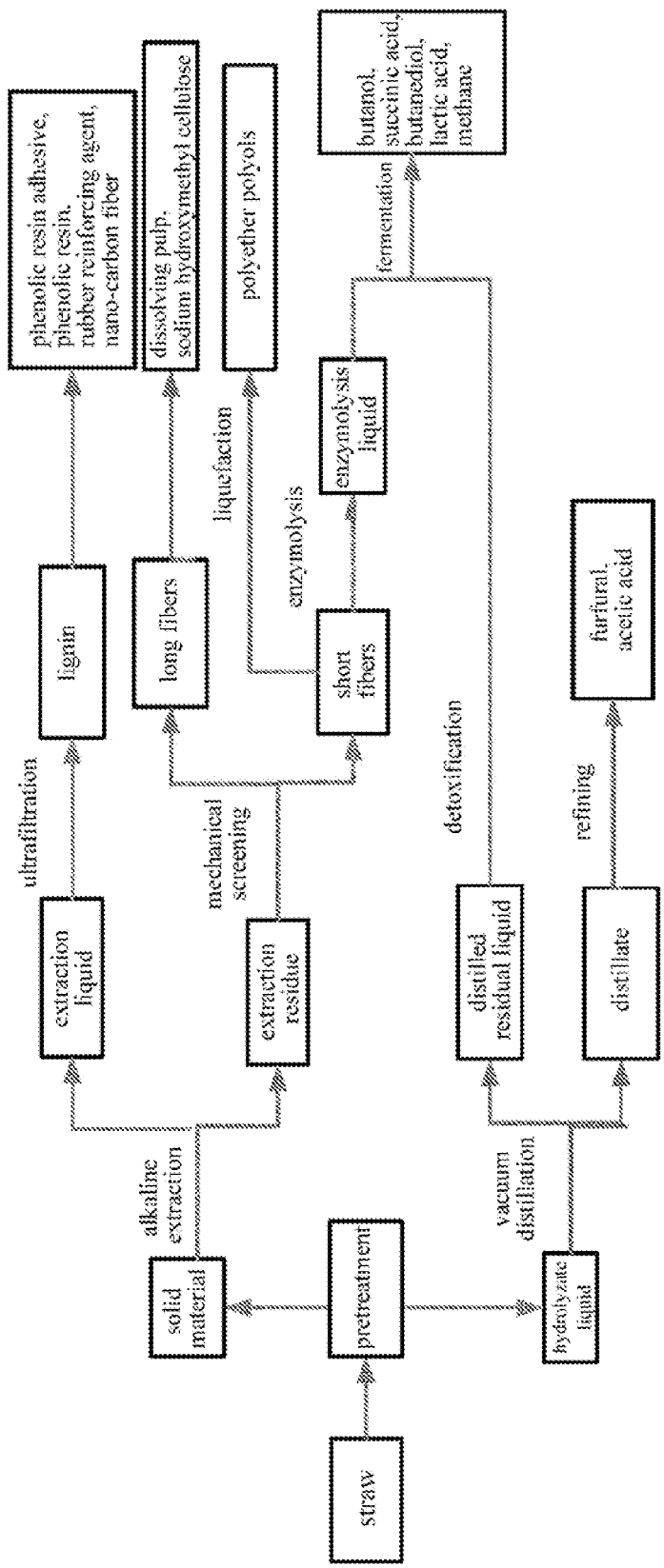
FIG. 1 is a diagram showing the preparation of bio-based products through degradation of straw hemicellulose using the method of the invention and the full utilization of the straw components, wherein corn straw are used as the example.

The lignin obtained in the above step can be used for the production of phenolic resin adhesive, a phenolic resin, a rubber reinforcing agent, and a nano-carbon fiber. The long fibers obtained in the above step can, after liquefaction, be used for the production of dissolving pulp, microcrystalline cellulose, and sodium hydroxymethyl cellulose. The short fibers obtained in the above step can, after liquefaction, be used for the production of polyether polyols. A sugar solution is obtained after bio-enzymolysis of the short fibers, and can be used in the production of a variety of fermentation products (see FIG. 1 for the specific process routes).

Accordingly, in another embodiment of the method of the present invention, the solid material obtained by the method of the present invention is processed into one or more of lignin, the long fibers and short fibers, wherein the lignin is further processed into industrial derivatives which is one or more selected from the group consisting of phenolic resin adhesive, a phenolic resin, a rubber reinforcing agent, and nano-carbon fiber; the long fibers and short fibers are further processed into sodium hydroxymethyl cellulose, polyether polyol and fermentation products. In a preferred embodiment, the fermentation products include butanol, succinic acid, butanediol, lactic acid, methane and hydrogen.

The method of the present invention is further explained in detail below in reference to the detailed Examples. It should be understood that the following Examples are only intended to illustrate the present invention, rather than to limit the scope of the present invention. In addition, unless otherwise specified, the raw materials and reagents used in the present invention are commercially available.

Example 1

One ton of air-dried corn straw (its water content is less than 5 wt %) was cut into 5-10 cm pieces by a cutting machine. Water at 15° C. was added to the straw pieces, and the straw pieces were soaked in the water for 60 min, wherein the mass ratio of straw to water was 1:1. Then the wet straw material was fed into a steam-explosion tank in a size of 11 m$^3$, and processed at a pressure of 0.3 MPa for 10 mins to generate a steam-exploded wet straw material. The steam-exploded wet straw material was then fed into an acid-hydrolysis tank in a size of 80 m$^3$, and hydrolyzed with 0.8 wt % sulfuric acid, wherein the mass ratio of the steam-exploded straw to the acid was 1:2, the hydrolysis temperature was 75° C. The reaction was performed for 60 mins. Then, the steam-exploded straw and hydrolyzate liquid from the hydrolysis tank were fed into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 75% (see Table 1).

Example 2

This Example was carried out in a substantially same manner as in Example 1, except that the straw was soaked in water at 50° C. for 30 mins; the mass ratio of straw to water was 1:2; the processing conditions for the steam explosion included a 0.8 Mpa pressure for 5 minutes; acid treatment conditions included a 30 mins reaction between 1.2 wt % of sulfuric acid and the steam-exploded straw at 90° C., wherein the mass ratio of the steam-exploded straw to the acid was 1:5.

The steam-exploded straw and hydrolyzate liquid from the hydrolysis tank were fed into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 82% (see Table 1).

Example 3

This Example was carried out in a substantially same manner as in Example 1, except that the straw was soaked in water at 90° C. for 10 mins; the mass ratio of straw to water was 1:3; the processing conditions for the steam explosion included a 2 Mpa pressure for 1 minutes; acid treatment conditions included a 10 mins reaction between 1.6 wt % of sulfuric acid and the steam-exploded straw at 105° C., wherein the mass ratio of the steam-exploded straw to the acid was 1:7.

The steam-exploded straw and hydrolyzate liquid from the hydrolysis tank were fed into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 90% (see Table 1).

Comparative Example 1

One ton of air-dried corn straw (its water content is less than 5 wt %) was cut into 5-10 cm pieces by a cutting machine. Water at 90° C. was added to the straw pieces, and the straw pieces were soaked in the water for 10 mins, wherein the mass ratio of straw to water was 1:3. Then the wet straw material was fed into a steam-explosion tank in a size of 11 m$^3$, and processed at a pressure of 2 MPa for 1 min to generate a steam-exploded wet straw material. The steam-exploded straw and hydrolyzate liquid from the hydrolysis tank were fed into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded straw reached 60% (see Table 1).

Example 4

One ton of air-dried corn straw (its water content is less than 5 wt %) was cut into 5-10 cm pieces by a cutting machine. Then 0.01 wt % of sulfuric acid was added to the straw pieces, and the straw pieces were soaked in the sulfuric acid for 10 mins, wherein the mass ratio of straw to acid was 1:1. Then the wet straw material was fed into a steam-explosion tank in a size of 11 m$^3$, and processed at a pressure of 0.3 MPa for 0.5 min to generate a steam-exploded wet straw material. The steam-exploded wet straw material was then added to and soaked in water in the weight equal to 4 times of that of the original straw material at 70° C. for 30 mins. Subsequently, the steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 60% (see Table 2).

Example 5

This Example was carried out in a substantially same manner as in Example 4, except that the straw was soaked in 0.04 wt % of sulfuric acid for 30 mins; the mass ratio of straw to acid was 1:2; the condition for the steam explosion included obtaining of a steam-exploded wet straw material under a 0.6 Mpa pressure for 2 minutes; the conditions for the product collection included soaking the steam-exploded wet straw material in water in the weight equal to 7 times of that of the original straw material at 70° C. for 45 mins.

The steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 78% (see Table 2).

Example 6

This Example was carried out in a substantially same manner as in Example 4, except that the straw was soaked in 0.1 wt % of sulfuric acid for 60 mins; the mass ratio of straw to acid was 1:3; the condition for the steam explosion included obtaining of a steam-exploded wet straw material under a 1.0 Mpa pressure for 3 minutes; the conditions for the product collection included soaking the steam-exploded wet straw material in water in the weight equal to 10 times of that of the original straw material at 70° C. for 10 mins.

The steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 85% (see Table 2).

Comparative Example 2

One ton of air-dried corn straw (its water content is less than 5 wt %) was cut into 5-10 cm pieces by a cutting machine. Then 0.1 wt % of sulfuric acid was added to the straw pieces, and the straw pieces were soaked in the sulfuric acid for 60 mins, wherein the mass ratio of straw to acid was 1:3. The wet straw material was then added to and soaked in water in the weight equal to 10 times of that of the original straw material at 70° C. for 10 mins. Subsequently, the wet straw material was extruded using an extruder to separate and obtain a straw hydrolyzate liquid and a straw solid material. The contents of cellulose, hemicellulose and lignin in the straw solid material were measured. Compared with the chemical composition of the original straw, the degradation rate of the hemicellulose in the acid-treated straw was 3% (see Table 2).

TABLE 1

Degradation after water immersion, steam explosion treatment in combination with acid treatment

| Example No. | Pretreatment | | | Steam explosion treatment | | Acid treatment | | | Degradation rate of hemicellulose |
|---|---|---|---|---|---|---|---|---|---|
| | Soaking solution | Mass ratio of straw to soaking solution | Soaking condition | Steam-explosion pressure | Pressure maintenance period | Acid concentration (wt %) | Mass ratio of steam-exploded straw to acid | Reaction condition | |
| Ex. 1 | water | 1:1 | 15° C., 60 min | 0.3 MPa | 10 min | 0.8% sulfuric acid | 1:2 | 75° C., 60 min | 75% |
| Ex. 2 | water | 1:2 | 50° C., 30 min | 0.8 MPa | 5 min | 1.2% sulfuric acid | 1:5 | 90° C., 30 min | 82% |
| Ex. 3 | water | 1:3 | 90° C., 10 min | 2 MPa | 1 min | 1.6% sulfuric acid | 1:7 | 105° C., 10 min | 90% |
| Com. Ex. 1 | water | 1:3 | 90° C., 10 min | 2 MPa | 1 min | — | — | — | 60% |

TABLE 2

Degradation after acid immersion in combination with steam explosion treatment

| Example No. | Pretreatment | | | Steam explosion treatment | | Product collection | | Degradation rate of hemicellulose |
|---|---|---|---|---|---|---|---|---|
| | Soaking solution (wt %) | Mass ratio of straw to soaking solution | Soaking condition | Steam-explosion pressure | Pressure maintenance period | Mass ratio of steam-exploded straw to water | Soaking condition | |
| Ex. 4 | 0.01% sulfuric acid | 1:1 | 15° C., 10 min | 0.3 MPa | 0.5 min | 1:4 | 70° C., 30 min | 60% |
| Ex. 5 | 0.04% sulfuric acid | 1:2 | 15° C., 30 min | 0.6 MPa | 2 min | 1:7 | 70° C., 45 min | 78% |
| Ex. 6 | 0.1% sulfuric acid | 1:3 | 15° C., 60 min | 1.0 MPa | 3 min | 1:10 | 70° C., 10 min | 85% |
| Com. Ex. 2 | 0.1% sulfuric acid | 1:3 | 15° C., 60 min | — | — | 1:10 | 70° C., 60 min | 3% |

As seen in Table 1, the conditions for the pretreatment and steam explosion treatment of straw were the same in Comparative Example 1 and Example 3, but the steam-exploded straw was not subjected to an acid treatment in Comparative Example 1. In Comparative Example 1, the degradation rate of the hemicellulose in the steam-exploded straw reached 60%, whereas in Example 3, the degradation rate of the hemicellulose in the steam-exploded and acid-treated straw reached 90%. From the comparison of the degradation rate of the hemicellulose in Examples 1~3 and in Comparative Example 1, it was demonstrated that the degradation rate of the hemicellulose was higher after the straw was subjected to water immersion, steam explosion treatment in combination with acid treatment than to water immersion and steam explosion treatment only.

As seen in Table 2, the conditions for the pretreatment (i.e. acid soaking) of straw were the same in Example 6 and Comparative Example 2, but the acid-soaked straw was not subjected to a steam explosion treatment in Comparative Example 2. In Comparative Example 2, the degradation rate of the hemicellulose in the acid-soaked straw was 3%, whereas in Example 6, the degradation rate of the hemicellulose in the steam-exploded and acid-soaked straw reached 85%. From the comparison of the degradation rate of the hemicellulose in Examples 4~6 and in Comparative Example 2, it was demonstrated that the degradation rate of the hemicellulose was higher after the straw was subjected to acid soaking in combination with steam explosion treatment than to acid soaking only.

Example 7

One ton of air-dried corn straw (its water content is less than 5 wt %) was cut into 5-10 cm pieces by a cutting machine. Water at 15° C. was added to the straw pieces, and the straw pieces were soaked in the water for 60 mins, wherein the mass ratio of straw to water was 1:1. Then the wet straw material was fed into a steam-explosion tank in a size of 11 m$^3$, and processed at a pressure of 0.8 MPa for 4 mins to generate a steam-exploded wet straw material. The steam-exploded wet straw material was then fed into an acid-hydrolysis tank in a size of 80 m$^3$, and hydrolyzed with 1.6 wt % hydrochloric acid, wherein the mass ratio of the steam-exploded straw to the acid was 1:2, the hydrolysis temperature was 105° C. After 60 mins reaction, the steam-exploded straw and hydrolyzate liquid were fed from the acid-hydrolysis tank into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 85%.

Example 8

One ton of air-dried corn straw (its water content is less than 5 wt %) was cut into 5-10 cm pieces by a cutting machine. Then 0.1 wt % of hydrochloric acid was added to the straw pieces, and the straw pieces were soaked in the sulfuric acid for 30 mins, wherein the mass ratio of straw to acid was 1:1. Then the wet straw material was fed into a steam-explosion tank in a size of 11 m$^3$, and processed at a pressure of 1.0 MPa for 3 mins to generate a steam-exploded wet straw material. The steam-exploded wet straw material was then added to and soaked in water in the weight equal to 10 times of that of the original straw material at 70° C. for 30 mins. Subsequently, the steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 75%.

Example 9

One ton of air-dried corn straw (its water content is less than 5 wt %) was cut into 5-10 cm pieces by a cutting machine. Water at 15° C. was added to the straw pieces, and the straw pieces were soaked in the water for 60 mins, wherein the mass ratio of straw to water was 1:1. Then the wet straw material was fed into a steam-explosion tank in a size of 11 m$^3$, and processed at a pressure of 0.8 MPa for 4 mins to generate a steam-exploded wet straw material. The steam-exploded wet straw material was then fed into an acid-hydrolysis tank in a size of 80 m$^3$, and hydrolyzed with 1.6 wt % phosphoric acid, wherein the mass ratio of the steam-exploded straw to the acid was 1:2, the hydrolysis temperature was 105° C. After 20 mins reaction, the steam-exploded straw and hydrolyzate liquid were fed from the acid-hydrolysis tank into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 82%.

Example 10

One ton of air-dried corn straw (its water content is less than 5 wt %) was cut into 5-10 cm pieces by a cutting machine. Then 0.1 wt % of phosphoric acid was added to the straw pieces, and the straw pieces were soaked in the phosphoric acid for 30 mins, wherein the mass ratio of straw to acid was 1:1. Then the wet straw material was fed into a steam-explosion tank in a size of 11 m$^3$, and processed at a pressure of 1.0 MPa for 3 mins to generate a steam-exploded wet straw material. The steam-exploded wet straw material was then added to and soaked in water in the weight equal to 10 times of that of the original straw material at 70° C. for 30 mins. Subsequently, the steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 69%.

Example 11

One ton of air-dried corn straw (its water content is less than 5 wt %) was cut into 5-10 cm pieces by a cutting machine. Water at 15° C. was added to the straw pieces, and the straw pieces were soaked in the water for 60 mins, wherein the mass ratio of straw to water was 1:1. Then the wet straw material was fed into a steam-explosion tank in a size of 11 m$^3$, and processed at a pressure of 1.3 MPa for 4 mins to generate a steam-exploded wet straw material. The steam-exploded wet straw material was then fed into an acid-hydrolysis tank in a size of 80 m³, and hydrolyzed with 1.0 wt % nitric acid, wherein the mass ratio of the steam-exploded straw to the acid was 1:2, the hydrolysis temperature was 105° C. After 60 mins reaction, the steam-exploded straw and hydrolyzate liquid were fed from the acid-hydrolysis tank into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 85%.

Example 12

One ton of air-dried corn straw (its water content is less than 5 wt %) was cut into 5-10 cm pieces by a cutting machine. Then 0.1 wt % of nitric acid was added to the straw pieces, and the straw pieces were soaked in the sulfuric acid for 30 mins, wherein the mass ratio of straw to acid was 1:1. Then the wet straw material was fed into a steam-explosion tank in a size of 11 m³, and processed at a pressure of 1.0 MPa for 3 mins to generate a steam-exploded wet straw material. The steam-exploded wet straw material was then added to and soaked in water in the weight equal to 10 times of that of the original straw material at 70° C. for 30 mins. Subsequently, the steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 72%.

Example 13

One ton of air-dried corn straw (its water content is less than 5 wt %) was cut into 5-10 cm pieces by a cutting machine. Water at 15° C. was added to the straw pieces, and the straw pieces were soaked in the water for 60 mins, wherein the mass ratio of straw to water was 1:1. Then the wet straw material was fed into a steam-explosion tank in a size of 11 m³, and processed at a pressure of 1.3 MPa for 4 mins to generate a steam-exploded wet straw material. The steam-exploded wet straw material was then fed into an acid-hydrolysis tank in a size of 80 m³, and hydrolyzed with a 1.0 wt % acid mixture (the mass ratio of sulfuric acid to phosphoric acid was 4:3 in the acid mixture), wherein the mass ratio of the steam-exploded straw to the acid was 1:2, the hydrolysis temperature was 105° C. After 60 mins reaction, the steam-exploded straw and hydrolyzate liquid were fed from the acid-hydrolysis tank into a plate filter to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 85%.

Example 14

One ton of air-dried corn straw (its water content is less than 5 wt %) was cut into 5-10 cm pieces by a cutting machine. Then a 0.1 wt % acid mixture (the mass ratio of sulfuric acid to hydrochloric acid was 1:1 in the acid mixture) was added to the straw pieces, and the straw pieces were soaked in the acid for 30 mins, wherein the mass ratio of straw to acid was 1:1. Then the wet straw material was fed into a steam-explosion tank in a size of 11 m³, and processed at a pressure of 1.0 MPa for 3 mins to generate a steam-exploded wet straw material. The steam-exploded wet straw material was then added to and soaked in water in the weight equal to 10 times of that of the original straw material at 70° C. for 30 mins. Subsequently, the steam-exploded wet straw material was extruded using an extruder to separate and obtain a steam-exploded straw hydrolyzate liquid and a steam-exploded straw solid material. The contents of cellulose, hemicellulose and lignin in the steam-exploded straw solid material were measured. Compared with the chemical composition of the original straw, the degradation rate of the hemicellulose in the steam-exploded and acid-treated straw reached 72%.

Example 15

The purpose of this Example is to demonstrate use of the hydrolyzate liquid obtained after the degradation of straw for butanol fermentation, wherein the straw was processed in the same manner as in Example 2.

The steam-exploded straw hydrolyzate liquid separated and obtained through the plate filter was distilled under a reduced pressure of 0.9 MPa and at 70° C. The distillate was collected and rectified. Then 1.1 kg of furfural and 3.3 kg of acetic acid were obtained.

The sugar solution that was distilled under a reduced pressure first passed through an electrodialysis device to separate acid radical ions therein, wherein the separation conditions included a temperature of 15° C. and a current density of 600 A/m². Then, the sugar solution passed through macroporous resin (AB-8, The Chemical Plant of Nankai University, Tianjin) to remove pigment in the sugar solution, wherein the separation conditions included a volume ratio of 1:5 between the sugar solution and the resin and a processing period of 12 hours. Finally, soluble lignin was removed from the sugar solution using activated carbon, wherein the separation conditions included a volume ratio of 1:5 between the sugar solution and the activated carbon (GH-6, Guanghua Jingke Activated Carbon Co., Ltd.) and a processing period of 12 hours. The sugar solution processed as above was used as the carbon source, wherein the concentration of sugar (glucose and xylose) was 50 g/L. Ammonium acetate was used as the nitrogen source. Then trace elements were added to prepare the fermentation medium. The proportion of the carbon source to nutrients was 1:10. The fermentation medium was adjusted to pH6.5 using NaOH, and sterilized at 121° C. for 10 mins.

*C. acetobutylicum* ATCC824 was inoculated into 7% (v/v) corn medium, cultured at 37° C. in an anaerobic condition for 24 hours, and after complete floating of the mash cover, transferred to the fermentation medium. The inoculation solution and the fermentation broth are in a volume ratio of 1:10. After the anaerobic culture at 37° C. for 72 hours, fermentation mash having a total solvent content of 22 g/L was obtained in the fermentation broth, wherein the concentration of butanol was 15 g/L.

Example 16

The purpose of this Example is to demonstrate use of the hydrolyzate liquid obtained after the degradation of straw for butanol fermentation, wherein the straw was processed in the same manner as in Example 5.

The steam-exploded straw hydrolyzate liquid separated and obtained through the extruder was distilled under a reduced pressure of 0.9 MPa and at 70° C. The distillate was collected and rectified. Then 2.1 kg of furfural and 5.2 kg of acetic acid were obtained.

The sugar solution that was distilled under a reduced pressure first passed through an electrodialysis device to separate acid radical ions therein, wherein the separation conditions included a temperature of 15° C. and a current density of 1000 A/m$^2$. Then, the sugar solution passed through macroporous adsorption resin (S-8, Anhui Sanxing Resin Technology Co., Ltd.,) to remove pigment in the sugar solution, wherein the separation conditions included a volume ratio of 1:7 between the sugar solution and the resin and a processing period of 8 hours. Finally, soluble lignin was removed from the sugar solution using activated carbon, wherein the separation conditions included a volume ratio of 1:10 between the sugar solution and the activated carbon (GH-6, Guanghua Jingke Activated Carbon Co., Ltd.) and a processing period of 12 hours. The sugar solution processed as above was used as the carbon source, wherein the concentration of sugar (glucose and xylose) was 80 g/L. Peptone was used as the nitrogen source. Then trace elements were added to prepare the fermentation medium. The proportion of the carbon source to nutrients was 1:8. The fermentation medium was adjusted to pH6.5 using NaOH, and sterilized at 121° C. for 10 mins.

The seed medium for Klebsiella sp. LN145 contained yeast extract 2.0 g/L, peptone 5.0 g/L, NaCl 5.0 g/L, malt extract 1.5 g/L, and glucose 20 g/L. Klebsiella sp. LN145 in the logarithmic growth phase was inoculated into the fermentation medium, wherein the inoculation amount was 10% (v/v). After an aerobic culture at 30° C. for 96 hours, the concentration of 2,3-butanediol was 34.4 g/L in the fermentation broth.

Example 17

The purpose of this Example is to demonstrate use of the hydrolyzate liquid obtained after the degradation of straw for butanol fermentation, wherein the straw was processed in the same manner as in Example 3.

The steam-exploded straw hydrolyzate liquid separated and obtained through the plate filter was distilled under a reduced pressure of 0.9 MPa and at 70° C. The distillate was collected and rectified. Then 1.5 kg of furfural and 3.9 kg of acetic acid were obtained.

The sugar solution that was distilled under a reduced pressure first passed through an electrodialysis device to separate acid radical ions therein, wherein the separation conditions included a temperature of 30° C. and a current density of 800 A/m$^2$. Then, the sugar solution passed through macroporous adsorption resin (Amberlite XAD-4, USA) to remove pigment in the sugar solution, wherein the separation conditions included a volume ratio of 1:7 between the sugar solution and the resin and a processing period of 8 hours. Finally, soluble lignin was removed from the sugar solution using activated carbon(GH-6, Guanghua Jingke Activated Carbon Co., Ltd.), wherein the separation conditions included a volume ratio of 1:10 between the sugar solution and the activated carbon and a processing period of 12 hours. The straw hemicellulose degradation liquid obtained from the above processing was used as the carbon source, wherein the concentration of sugar (glucose and xylose) was 100 g/L. Peptone was used as the nitrogen source. Then trace elements were added to prepare the fermentation medium. The proportion of the carbon source to nutrients was 1:8. The fermentation medium was adjusted to pH6.5 using NaOH, and sterilized at 121° C. for 10 mins.

The seed medium for Lactobacillus sp ZJU-1 contained 10 ml of malt juice (10° Brix) and 1 g of CaCO$_3$, and was sterilized at 115° C. for 20 mins. Lactobacillus sp ZJU-1 in the logarithmic growth phase was inoculated into the fermentation medium, wherein the inoculation amount was 10% (v/v). After an aerobic culture at 30° C. for 96 hours, the concentration of lactic acid was 88 g/L in the fermentation broth.

Example 18

The purpose of this Example is to demonstrate use of the hydrolyzate liquid obtained after the degradation of straw for butanol fermentation, wherein the straw was processed in the same manner as in Example 6.

The steam-exploded straw hydrolyzate liquid separated and obtained through the plate filter was distilled under a reduced pressure of 0.9 MPa and at 70° C. The distillate was collected and rectified. Then 2.5 kg of furfural and 5.3 kg of acetic acid were obtained.

The sugar solution that was distilled under a reduced pressure first passed through an electrodialysis device to separate acid radical ions therein, wherein the separation conditions included a temperature of 30° C. and a current density of 1000 A/m$^2$. Then, the sugar solution passed through macroporous adsorption resin (Amberlite XAD-6, USA) to remove pigment in the sugar solution, wherein the separation conditions included a volume ratio of 1:3 between the sugar solution and the resin and a processing period of 8 hours. Finally, soluble lignin was removed from the sugar solution using activated carbon(GH-6, Guanghua Jingke Activated Carbon Co., Ltd.), wherein the separation conditions included a volume ratio of 1:3 between the sugar solution and the activated carbon and a processing period of 12 hours. The sugar solution processed as above was used as the carbon source, wherein the concentration of sugar (glucose and xylose) was 20 g/L. Peptone was used as the nitrogen source. Then trace elements were added to prepare the fermentation medium. The proportion of the carbon source to nutrients was 1:8. The fermentation medium was adjusted to pH6.5 using NaOH, and sterilized at 121° C. for 10 mins.

Activated sludge was obtained from the Gaobeidian Sewage Plant, Beijing. The activated sludge was added directly to the fermentation medium, and the inoculation amount was 10% (v/v). The anaerobic fermentation was carried out for 10 d. One liter of methane was collected from each liter of the fermentation medium.

Example 19

The purpose of this Example is to demonstrate use of the hydrolyzate liquid obtained after the degradation of straw for butanol fermentation, wherein the straw was processed in the same manner as in Example 1.

The steam-exploded straw hydrolyzate liquid separated and obtained through the plate filter was distilled under a reduced pressure of 0.9 MPa and at 70° C. The distillate was collected and rectified. Then 1.1 kg of furfural and 3.3 kg of acetic acid were obtained.

The sugar solution that was distilled under a reduced pressure first passed through an electrodialysis device to separate acid radical ions therein, wherein the separation conditions included a temperature of 15° C. and a current density of 600 A/m$^2$. Then, the sugar solution passed through anion exchange resin (HZ-803, Huazhen Technology Company, Shanghai) to remove salt ions in the sugar solution, wherein the separation conditions included a volume ratio of 1:10 between the sugar solution and the resin and a processing period of 12 hours. Finally, soluble lignin was removed from the sugar solution using activated carbon (GH-6, Guanghua Jingke Activated Carbon Co., Ltd.), wherein the separation conditions included a volume ratio of 1:10 between the sugar solution and the activated carbon and a processing period of 12 hours. The straw hemicellulose degradation liquid obtained from the above processing was used as the carbon source, wherein the concentration of sugar (glucose and xylose) was 40 g/L. Ammonium acetate was used as the nitrogen source. Then trace elements were added to prepare the fermentation medium. The proportion of the carbon source to nutrients was 1:8. The fermentation medium was adjusted to pH6.5 using NaOH, and sterilized at 121° C. for 10 mins.

The seed medium for *Clostridium butyrium AS*1.209 contained glucose 20 g/L, yeast extract 0.5 g/L, $KH_2PO_4$ 0.2 g/L, $K_2HPO_4$ 1.6 g/L, $MgSO_4.7H_2O$ 0.2 g/L, NaCl 0.1 g/L, $CaCl_2$ 0.01 g/L, $Na_2S.9H_2O$ 0.25 g/L, $NaMoO_4.2H_2O$ 0.01 g/L, $NaHCO_3$ 0.2 g/L and $(NH_4)_2SO_4$ 3.0 g/L, and was sterilized at 115° C. for 15 mins. *Clostridium butyrium* AS1.209 in the logarithmic growth phase was inoculated into the fermentation medium, wherein the inoculation amount was 10% (v/v). After an anaerobic culture at 37° C. for 60 hours, 0.5 L of hydrogen was collected from each liter of the fermentation medium.

Example 20

The purpose of this Example is to demonstrate use of the solid material obtained after the degradation of straw for the production of industrial derivatives, wherein the straw was processed in the same manner as in Example 1.

The solid material obtained by squeezing the steam exploded straw was fed to an alkaline extraction tank. A 2 wt % NaOH solution was added and kept at a temperature of 150° C. for 4 hours. The solid material was extruded by an extruder, so as to obtain an alkaline extraction liquid and an alkaline extraction residue; the extraction liquid passed through a PVC ultrafiltration membrane to recover NaOH. The solid material obtained by the ultrafiltration was collected and dried to obtain lignin. The lignin was used for the production of phenolic resin adhesive, phenolic resin, rubber reinforcing agent, nano-carbon fiber. The alkaline extraction residue passed through a mechanical carding machine to separate long fibers and short fibers, wherein the long fibers were used for the production of sodium hydroxymethyl cellulose and polyether polyols and the short fibers were degraded into glucose while cellulase was added.

The invention claimed is:

1. A process for producing a bio-based product from straw hemicellulose, comprising the steps of:

1) pretreating straw, wherein the straw is soaked in water, wherein a mass ratio of straw to water is from 1:1 to 1:3, a soaking temperature is from 15° C. to 90° C., and a soaking period is from 10 mins to 60 mins;
2) conducting steam explosion, wherein the straw soaked in step 1) is fed into a steam-explosion tank, and maintained under a steam-explosion pressure for a steam-explosion period; then a steam-exploded straw material is released, wherein a steam-explosion pressure is from 0.3 MPa to 2.0 MPa, and a pressure maintenance period is from 1 min to 10 mins;
3) performing an acid treatment, wherein the steam-exploded straw material obtained in step 2) is fed into an acid-hydrolysis tank pre-filled with a 0.8 to 1.6 wt % dilute acid and subjected to acid hydrolysis to generate a hydrolyzed material, wherein in the acid-hydrolysis tank, a mass ratio of the steam-exploded straw to the dilute acid is from 1:2 to 1:7, a reaction temperature is from 75° C. to 105° C., and a reaction time is from 10 mins to 60 mins; and
4) collecting the product thus obtained, wherein after the acid hydrolysis in step 3), the hydrolyzed material obtained in step 3) is filtered to generate a hydrolyzate liquid, and a hydrolysis residue is collected and extruded using an extruder to obtain a solid material.

2. The process according to claim 1, characterized in that said dilute acid is one or more selected from the group consisting of dilute sulfuric acid, dilute hydrochloric acid, dilute nitric acid, and dilute phosphoric acid.

3. The process according to claim 1, characterized in that said straw is one or more selected from corn straw, rice straw, wheat straw, bagasse, corn cobs, sorghum straw, *miscanthus sinensis, imperata cylindrica*, ramie, jute, abutilon, marijuana, flax, Apocynum, kenaf, cotton stalks, banana stems, pineapple leaf, and *ponnisetum hydridum.*

4. The process according to claim 1, further comprising the steps of:

a) distilling the hydrolyzate liquid obtained from the step 4) in claim 1 under a reduced pressure, collecting and refining a distillate to obtain furfural and acetic acid, wherein a distilled residue liquid is a sugar solution at a concentration of 20 g/L-150 g/L by weight of xylose and glucose; and
b) preparing a fermentation medium from the sugar solution obtained in step a) by adding a nitrogen source therein after detoxification treatment, inoculating a seed solution of a fermentation bacterium in the logarithmic growth phase at a concentration of 10% by weight of the fermentation medium to produce a fermentation product, wherein the detoxification treatment is one or more selected from the group consisting of electrodialysis, macroporous resin adsorption, and activated carbon adsorption, the nitrogen source is one or more selected from the group consisting of corn milk, corn extracts, yeast extract, peptone, $(NH_4)_2HPO_4$, $(NH_4)_2SO_4$, and ammonium acetate, and the fermentation bacterium is *Clostridium acetobutyliucm, Actinobacillus succinogenes, Klebsiella, Lactobacillus*, or *Clostridium butyricum.*

5. The process according to claim 4, characterized in that the processing condition for the electrodialysis includes a temperature of 15 to 30° C. and a current density of 600-1000 $A/m^2$; a processing condition for the macroporous resin adsorption includes a volume ratio of 1:3 to 1:10 between the sugar solution and a macroporous resin and a processing period of 4-12 hours; a processing condition for the activated carbon adsorption includes a volume ratio of 1:3 to 1:10 between the sugar solution and an activated carbon and a processing period of 4-12 hours.

6. The process according to claim 1, characterized in that the obtained solid material is processed into one or more of lignin, long fibers, and short fibers.

7. The process according to claim 6, characterized in that the lignin is further processed into a chemical product, wherein the chemical product is one or more selected from the group consisting of, a phenolic resin, a rubber reinforcing agent, and a nano-carbon fiber.

8. The process according to claim 6, characterized in that the long fibers and short fibers are further processed into sodium hydroxymethyl cellulose, polyether polyol, and fermentation products.

9. The process according to claim 4, characterized in that the fermentation product includes butanol, succinic acid, butanediol, lactic acid, methane, and hydrogen.

10. The process according to claim 1, wherein the steam-explosion pressure is from 0.5 to 1.0 MPa.

11. The process according to claim 3, wherein said straw is one or more selected from the group consisting of corn straw, corn cobs, bagasse, and marijuana.

12. The process according to claim 7, wherein the phenolic resin is phenolic resin adhesive.

* * * * *